(12) United States Patent
Volker

(10) Patent No.: US 9,422,175 B2
(45) Date of Patent: Aug. 23, 2016

(54) CHLORINE MEASUREMENT/FILTER TESTING/BRINE CONTAINER MONITORING OF A WATER TREATMENT SYSTEM

(71) Applicant: Manfred Volker, Blankenbach (DE)

(72) Inventor: Manfred Volker, Blankenbach (DE)

( * ) Notice: Subject to any disclaimer, the term of this patent is extended or adjusted under 35 U.S.C. 154(b) by 211 days.

(21) Appl. No.: 14/049,722

(22) Filed: Oct. 9, 2013

(65) Prior Publication Data

US 2015/0014251 A1    Jan. 15, 2015

(30) Foreign Application Priority Data

Jul. 13, 2013 (DE) .......................... 10 2013 011 752

(51) Int. Cl.
| | |
|---|---|
| C02F 1/467 | (2006.01) |
| C02F 1/00 | (2006.01) |
| G01N 33/18 | (2006.01) |
| C02F 1/461 | (2006.01) |
| C02F 1/42 | (2006.01) |
| C02F 5/08 | (2006.01) |

(52) U.S. Cl.
CPC .............. *C02F 1/4674* (2013.01); *C02F 1/008* (2013.01); *C02F 1/4618* (2013.01); *G01N 33/18* (2013.01); *C02F 1/42* (2013.01); *C02F 5/08* (2013.01); *C02F 2201/46125* (2013.01); *C02F 2209/29* (2013.01); *C02F 2303/04* (2013.01); *C02F 2303/16* (2013.01); *C02F 2303/185* (2013.01)

(58) Field of Classification Search
CPC ...... C02F 1/4674; C02F 1/4618; C02F 1/008; G01N 33/18
See application file for complete search history.

(56) References Cited

U.S. PATENT DOCUMENTS

| 4,247,345 | A | * | 1/1981 | Kadija et al. ................. 156/73.4 |
| 4,329,215 | A | * | 5/1982 | Scoville ..................... 204/228.2 |
| 6,726,817 | B1 | * | 4/2004 | Gruett ........................... 204/400 |
| 7,604,720 | B2 | * | 10/2009 | Kaczur et al. ................. 204/258 |
| 2002/0195403 | A1 | * | 12/2002 | Takeda et al. ................. 210/749 |

FOREIGN PATENT DOCUMENTS

IT           1244040      *   7/1994

OTHER PUBLICATIONS

U.S. Appl. No. 14/049,708, filed Oct. 9, 2013, Chlorine Measurement/Filter/Brine Container Monitoring of Water Treatment System.
U.S. Appl. No. 14/049,714, filed Oct. 9, 2013, Chlorine Measurement/Filter/Brine Container Monitoring of Water Treatment System.

* cited by examiner

*Primary Examiner* — Chester Barry
(74) *Attorney, Agent, or Firm* — Greer, Burns & Crain, Ltd

(57) ABSTRACT

The water treatment system, particularly pre-filtration unit of the water treatment system, comprising at least one chlorine sensor device, is characterized in that the water treatment system contains a salt-water treatment device which is connected to the chlorine sensor device, an electrolysis cell being disposed in the associated line, and thereafter a pump and a release valve.

14 Claims, 2 Drawing Sheets

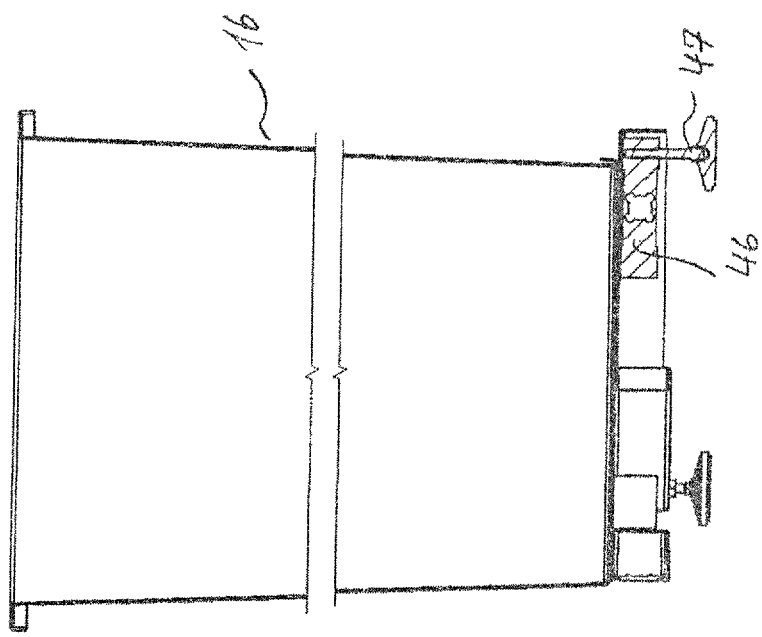
FIG. 2a
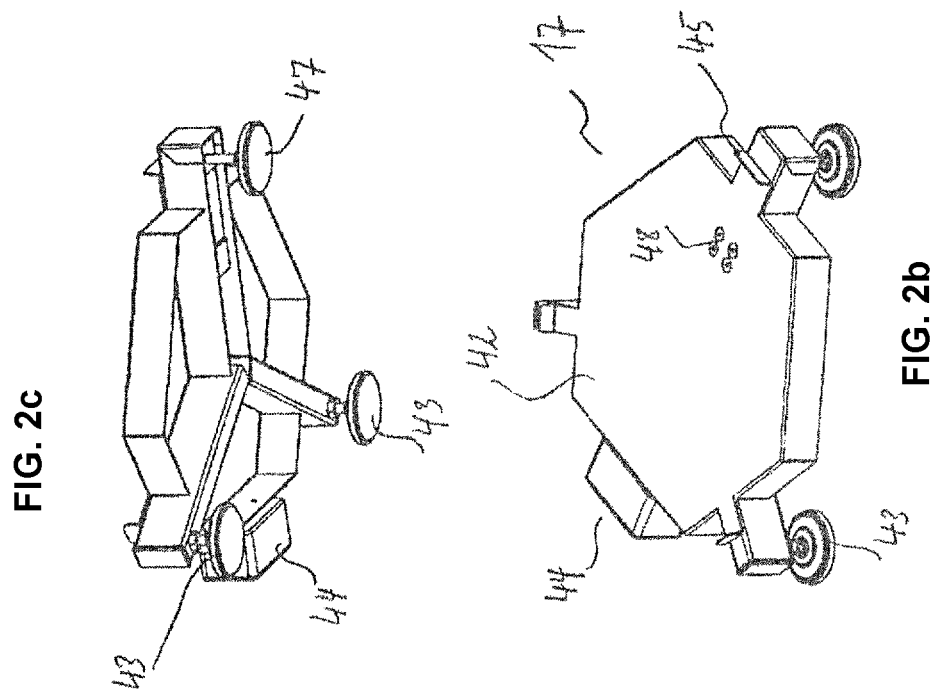
FIG. 2c
FIG. 2b

CHLORINE MEASUREMENT/FILTER TESTING/BRINE CONTAINER MONITORING OF A WATER TREATMENT SYSTEM

FIELD OF THE INVENTION

The present invention refers to a fluid system for quality/function monitoring and/or control of physically and chemically acting filter stages of a water pretreatment for the operation of a reverse-osmosis or another water treatment or water monitoring system.

BACKGROUND OF THE INVENTION

Filter routes have the disadvantage that the remote diagnosis of chlorine and hardness or the monitoring of the degree of soiling of mechanical filters, respectively, cannot be carried out or can only be carried out by taking great efforts.

Moreover, it is necessary for reasons of safety, particularly in dialysis water treatments, that a time-consuming manual documentation of the water hardness and/or of the chlorine content should be carried out daily, especially in order to furnish evidence that the toxic chlorine has been removed from the liquid by the filters used.

Existing chlorine sensors for online measurement are often not chlorinated at regular intervals and cannot provide any reliable measurement results in the absence of chlorine in the liquid.

To remove hardly soluble salts, such as calcium and/or magnesium, from the water, softeners are often used. When softeners are used with acidic cation exchange resins, these must be regenerated by means of sodium chloride brine solution at regular intervals.

This regeneration is normally carried out with sodium chloride solution which is provided in a so-called brine container in which salt is dissolved in a predetermined liquid amount. Failure of the regeneration process e.g. because of a missing sodium chlorine brine solution may lead to serious calcification of the downstream systems.

Moreover, softeners tend to show a microbial growth with subsequent contamination of the liquid flowing therethrough because of the relatively large resin volume.

Problems are posed by filter blocking because the resulting exchange of filter material is normally accompanied by operational interruption.

SUMMARY OF THE INVENTION

It is the aim of the invention to permit the development of an actuator-sensor control and software which enable the user to evaluate the functionality of a system by online access and to obtain, on this basis, a remote diagnosis about the current operational state.

To meet the normative and/or in-house requirements, the necessary documentation evidence can be furnished simultaneously together with the automatic recording by way of the connected electronic data processing system.

It is possible on account of the desired system-specific evaluation by analysis and visualization of the operational parameters to achieve an acyclic distribution of the service operations and thus a reduction of the number of services.

On this basis an economic and ecological procedure is possible as the deployment of trained stuff on site can thereby be coordinated in an improved way and failure caused by wear can be avoided in a targeted and preventive way.

To avoid the aforementioned drawbacks and to comply with the objective, respectively, partial streams are passed under one aspect of the present invention to the corresponding sensor before and after the filter stages by means of switched valves and are evaluated by electronic measuring devices. These measuring devices may here also be an integral part of subsequent systems of a water treatment and/or also a control room. A bidirectional operation for influencing actuators and sensors is here also possible.

Advantageously, with an electronic pressure sensor different mechanical filter stages are monitored online with respect to their degree of soiling by measuring the pressures and determining the pressure difference and an automatic backwashing program is also started in the case of suitable filters with a corresponding automatic backwashing system.

Under another aspect of the invention, use is made of an online measuring chlorine sensor the safety-relevant function of which is checked according to the invention by supplying electrolytically produced chlorine of a known concentration to the sensor at regular intervals. The measurement result is electronically recorded and documented. The chlorine can be produced from an existing brine solution.

The function of the softener, i.e. the filtration and reduction of the hardly soluble calcium and magnesium salts, can be monitored by an ion-sensitive calcium and/or magnesium sensor.

The fill level of the salt water container and the residual volume of the salts in the brine container, respectively, have to be monitored in a simple way by means of a weighing device. To this end the brine container is placed on a constructional element with weighing cell. Since the constructional understructure can advantageously be used at any time independently of the brine container used, brine containers that are already in use can also be equipped with the monitoring device.

It is possible to indicate the brine volume directly or as a signal-light solution with message color; transfer to and recording in a control room or a subsequent water treatment system, which may e.g. be configured as an RO system, is also possible. Inspection and documentation of the salt supply in the brine container which has to be carried out by the operating personnel daily can thus be dispensed with.

A regular slight chlorination of the softener during regeneration by chlorine which is electrolytically produced from the brine container of the softener reduces the microbial growth in the softener resin and thereby ensures a more sterile liquid.

BRIEF DESCRIPTION OF THE DRAWINGS

FIG. 2a is a cross-sectional view of a salt water container according to the invention.

FIG. 2b is a top perspective view of a weighing platform according to the invention.

FIG. 2c is a bottom perspective view the weighing platform of FIG. 2b.

DETAILED DESCRIPTION OF THE DRAWINGS

Figure 1:
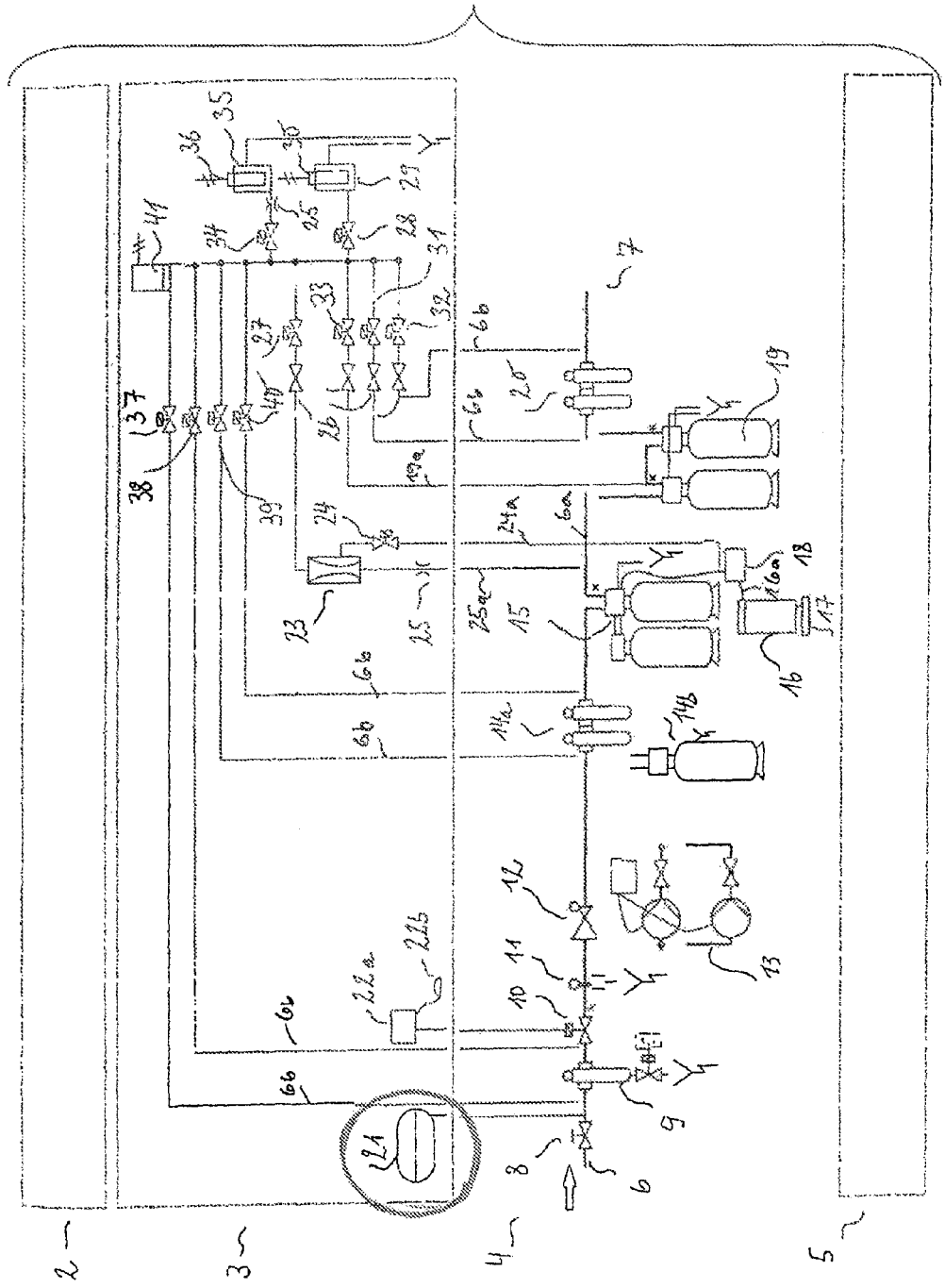
FIG. 1 is a schematic diagram of a pre-filtration unit according to the invention.

FIG. 1 shows a pre-filtration unit according to the invention with a mechanical-chemical filter stage (4), an actuator-sensor monitoring unit (3), an associated electronic evaluation unit (2), and a possible electronic unit (5) pertaining e.g. to a downstream reverse osmosis system, wherein the electronic unit (2) may also be configured as a control-room electronic and may communicate with the electronic unit (5).

The mechanical-chemical filter stage (4) is only shown by way of example with respect to the selection of the arranged filter stages so to as to illustrate the function of the monitoring operation according to the invention.

The exemplary arrangement begins with the water inlet (6), a shut-off valve (8), and an automatically back-washable pre-filter (9) with drain valve and drainage connection. This is followed by a safety shut-off valve (10) which is activated by a leakage indicator (22a) with liquid sensor (22b).

Further components may be a pipe separator (11) and a backflow preventer (12) for avoiding contamination of the water inlet (6).

At low water supply pressures it is possible to add a pressure increasing unit (13). A further filter stage (14) may be configured as a cartridge filter (14a), sand filter (14b) or also as a hollow fiber filter (here not shown) in the nano or ultra-pore range.

(15) shows a softener, e.g. illustrated as a twin softener, which is normally filled with strongly acidic, cation-containing resin which upon exhaustion has to be regularly regenerated with NaCl solution from the salt water treatment (16). It is here important to monitor the fill level of the salt in the salt water container (16). This is done with a weighing device (17), which is designed as an independent constructional understructure.

According to FIG. 2 the weighing device (17) consists of a weighing cell (46) the signal of which can be amplified by electronics (44) on the weighing platform (42), electronically processed, or can be processed by electronics (2) and also by possibly successive electronics (5). Preset weight limit values of the brine container can here be monitored and optically or acoustically indicated or remotely diagnosed by technical electronic data processing. The weighing cell (46) is fastened to the weighing platform (42) by means of screws (48) such that a third of the brine or salt weight weighs on the measuring foot (47). Side boundaries (45) are mounted for the lateral guidance of the brine container.

During the regeneration process of the softener (15) chlorine-containing solution can be formed with the help of the electrolysis device (18) from the salt water flowing towards the electrolysis cell. It goes without saying that the chlorine concentration depends on the brine concentration, but substantially on the magnitude of the electrically supplied power to the electrolysis cell. The microbial growth in the softener resin is thereby strongly reduced.

(19) shows a twin carbon filter/dechlorination device which is used for the filtration of the chlorine.

Filter stage (20) as a fine-filter stage can remove the smallest particles from the filter water (7) before it is e.g. supplied to a reverse osmosis system or a drinking water installation.

The actuator-sensor unit (3) can be equipped with an electronic water meter (21) for recording and reporting the water consumption.

For monitoring the chlorine content of the supplied liquid a chlorine sensor (30) is preferably positioned in a chlorine sensor chamber (29), either for the measurement of the whole chlorine or of the free chlorine. The chlorine sensor chamber (29) has an inlet and a free outlet. The release valve (28) is directly positioned in front of the sensor chamber. Usually, the supplied liquid can be chlorinated by the water supplier with chlorine of different concentrations; depending on the hygienic state, a chlorine input may be temporarily missing. In such a case no statement can thus be made on the proper function of the sensor (30).

For regularly checking the chlorine sensor the test valve (27), the brine suction valve (24), and the release valve (28) are opened and the electrolysis cell (18) is switched on. The brine or the chlorine-containing solution is sucked in a selected concentration ratio from the container (16) via the adjustable brine suction valve (24) and the pump (23), mixed with liquid via flow throttle (25), passed on to the measuring chamber (29), recorded via chlorine sensor (30) and evaluated with electronics (2) and (5), respectively.

The proper function of the measuring cell (30) is ensured by this regular testing.

It is within the meaning of the present invention to provide and monitor the sodium chloride brine solution also exclusively for the purpose of chlorine sensor monitoring, independently of a softener or other filter stages. The suction line of the brine solution and the electrolysis cell for the electrolytic chlorine production are here independent of the brine suction line and the electrolysis cell of the softener.

Pump (23) is shown by way of example as a venturi pump; other pump types are possible for performing the function; in such a case the chlorine-containing solution is supplied in metered amounts by means of a pump (not shown) from line 24a into line 25a.

For monitoring the correct carbon filter function/dechlorination device (19) a valve, e.g. (40) or (27), may first be opened. Likewise, release valve (28) is opened. If chlorine is contained in the supplied liquid, this is recorded via the previously verified chlorine sensor (30).

Thereupon, the valves (33), (31) or also (32) are successively opened; likewise, the chlorine release valve (28) is opened. For instance, the filter stages of the carbon filter can be tested. If the chlorine sensor records the absence of chlorine, the checking of the filter is successfully completed. It is within the meaning of the present invention that this measurement can also be carried out independently and recorded technically by electronic data processing.

For monitoring the filter stages (9), (14), (30) the pressure sensor (41) is acted upon selectively and successively before or after the filter stages with the pressures prevailing at the filter stages via the valves arranged in FIG. 1.

For instance, the pressure drop of the filter stage (9) is monitored by measuring the inlet pressure via valve (37) and the outlet pressure is monitored by the valve (38).

As an equivalent to the said measurement, FIG. 1 shows the measurement of the pressure drops by switching the valves (39/40) for the filter stage (14) and the valves (31/32) for filter stage (20).

A determination of the pressure drops at softening stage (15) and dechlorination stage (19) is also possible by way of a successive switching of the valves (40, 27, 33, 31).

An atmospheric relief of the pressure sensor (41) in general or between 2 measurements can be carried out via valve (34) and also (28).

By measurement of the flow through line 6 with water meter/flow meter (21) or also by a corresponding flow measurement in a subsequent treatment process, the pressure values measured on the filters can be calculated by means of electronics (2, 5) as standard or mean values and a warning, exchange, flushing or maintenance time can be predicted for preset pressure differences.

Since the determination of the filter pressure differences normally regards relative measurements, the use of a single pressure sensor (41) is advantageous both in terms of costs and in terms of the calibration efforts.

As a rule, the water inlet pressures on line (6), e.g. on filter (9), are known, so that the pressure sensor (41), acted upon with a known pressure before the beginning of a measurement cycle, must be verified during maintenance or during inspection by a technician.

An advantageous development of the pressure measurement is the determination of mean pressure values by means of electronics (2, 5) on the respective filters (9, 14, 15, 19, 20) in that e.g. 50 measurements are combined to form a mean value and are represented over an exemplary period of 1000 operating hours.

Changes that are due to the service life end of the sensor (41) or the blocking of the aforementioned filters can be recognized technically by electronic data processing or predicted, respectively, and remotely inquired.

To monitor the correct function of the softener (15), valve (40) is first of all opened and hard water is supplied over measuring chamber (35) to the calcium sensor (35) through the opened valve (34).

Subsequently, softened liquid is passed via flow throttle (25), valves (27, 34) into the measuring chamber (35) to the ion-sensitive calcium sensor (36).

LEGEND

| | |
|---|---|
| 1. | Pre-filtration with sensor package |
| 2. | Electronics sensor package |
| 3. | Actuator and sensor unit |
| 4. | Pre-filtration components |
| 5. | Electronics post-filtration |
| 6. | Water inlet |
| 7. | Filter water |
| 8. | Shut-off valve |
| 9. | Back-flushable pre-filter with cleaning valve |
| 10. | Safety shut-off valve |
| 11. | Pipe separator |
| 12. | Backflow preventer |
| 13. | Pressure increasing unit |
| 14. | Fine-filter stage 2 |
| 15. | Softening stage |
| 16. | Salt water treatment/brine tank |
| 17. | Weighing unit |
| 18. | Electrolysis cell |
| 19. | Dechlorination stage/carbon filter |
| 20. | Fine-filter stage 3 |
| 21. | Water meter/flow meter |
| 22. | Leakage indicator with sensor |
| 23. | Brine pump |
| 24. | Brine suction valve |
| 25. | Flow throttle |
| 26. | Backflow preventer |
| 27. | Chlorine sensor test valve/calcium check valve I |
| 28. | Chlorine sensor release valve |
| 29. | Chlorine sensor chamber |
| 30. | Chlorine sensor |
| 31. | Chlorine check valve II/fine-filter stage 3 inlet pressure |
| 32. | Chlorine check valve III/fine-filter stage 3 outlet pressure |
| 33. | Chlorine check valve I |
| 34. | Calcium sensor release valve |
| 35. | Calcium sensor chamber |
| 36. | Calcium sensor |
| 37. | Fine filter stage 1 inlet pressure |
| 38. | Fine filter stage 1 outlet pressure |
| 39. | Fine filter stage 2 inlet pressure |
| 40. | Fine filter stage 2 outlet pressure/calcium test valve |
| 41. | Pressure sensor |
| 6a | Lines |
| 6b | |
| 16a | |
| 19a | |
| 24a | |
| 25a | |
| 42. | Platform |
| 43. | Adjustable feet |
| 44. | Electronics |
| 45. | Side boundary |
| 46. | Weighing cell |
| 47. | Measurement foot |
| 48. | Mounting of weighing cell |

The invention claimed is:

1. A water treatment system, particularly pre-filtration unit of the water treatment system, comprising at least one chlorine sensor device, wherein the water treatment system contains a salt-water treatment device which is connected to the chlorine sensor device, an electrolysis cell being disposed in the associated line, and thereafter a pump and a release valve, wherein a softener device which has connected thereto the salt water treatment device via a salt water line, the electrolysis cell being disposed in the salt water line and a chlorine test line branching off between the electrolysis cell and the softening device, which leads to the at least one chlorine sensor device.

2. The water treatment system according to claim 1, wherein a water line in which an adjustable throttle is disposed leads to the pump.

3. The water treatment system according to claim 2, wherein the pump is a venturi pump.

4. The water treatment system according to claim 2, wherein the chlorine-containing solution is metered by means of the pump from the chlorine test line into the water line.

5. The water treatment system according to claim 1, wherein the chlorine sensor device comprises a sensor chamber and a chlorine sensor.

6. The water treatment system according to claim 5, wherein the chlorine sensor is connected to an electronic evaluation unit.

7. The water treatment system according to claim 5, wherein the release valve is positioned upstream of the sensor chamber, and that the sensor chamber has an outlet.

8. The water treatment system according to claim 1, wherein the salt treatment device comprises a salt water container which is arranged on a weighing device.

9. The water treatment system according to claim 1 wherein the softening device is a softener which is filled with strongly acidic cation-containing resin.

10. The water treatment system according to claim 1, wherein the magnitude of the electrical power of the electrolysis cell is adjustable by a control device.

11. The water treatment system according to claim 1, wherein a dechlorination device is disposed in the water line, the outputs of which are connected via lines and switching valves to the chlorine sensor device.

12. The water treatment system according to claim 1, wherein the water treatment system is a reverse osmosis system.

13. A water treatment system, particularly pre-filtration unit of the water treatment system, comprising at least one chlorine sensor device, wherein the water treatment system contains a salt-water treatment device which is connected to the chlorine sensor device, an electrolysis cell being disposed in the associated line, and thereafter a pump and a release valve, wherein a water line in which an adjustable throttle is disposed leads to the pump, and wherein the pump is a venturi pump.

14. A water treatment system, particularly pre-filtration unit of the water treatment system, comprising at least one chlorine sensor device, wherein the water treatment system contains a salt-water treatment device which is connected to the chlorine sensor device, an electrolysis cell being disposed in the associated line, and thereafter a pump and a release valve, wherein a dechlorination device is disposed in the water line, the outputs of which are connected via lines and switching valves to the chlorine sensor device.

\* \* \* \* \*